United States Patent
Nagae et al.

(10) Patent No.: US 9,585,629 B2
(45) Date of Patent: Mar. 7, 2017

(54) SUBJECT INFORMATION OBTAINING APPARATUS, METHOD FOR OBTAINING SUBJECT INFORMATION, AND COMPUTER-READABLE STORAGE MEDIUM

(75) Inventors: Kenichi Nagae, Yokohama (JP); Hirofumi Taki, Osaka (JP); Toru Sato, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 758 days.

(21) Appl. No.: 13/437,658

(22) Filed: Apr. 2, 2012

(65) Prior Publication Data
US 2012/0259218 A1 Oct. 11, 2012

(30) Foreign Application Priority Data
Apr. 8, 2011 (JP) ................................. 2011-086511

(51) Int. Cl.
*G01S 15/00* (2006.01)
*A61B 8/00* (2006.01)
(Continued)

(52) U.S. Cl.
CPC ............ *A61B 8/085* (2013.01); *A61B 8/0858* (2013.01); *A61B 8/486* (2013.01); *A61B 8/5207* (2013.01);
(Continued)

(58) Field of Classification Search
CPC .. G06F 3/043; G01S 15/8993; G01S 15/8977; G01S 15/8979; G01S 15/8988; A61B 8/488; G06T 2207/10132
See application file for complete search history.

(56) References Cited

U.S. PATENT DOCUMENTS

2003/0009102 A1* 1/2003 Quistgaard et al. .......... 600/446
2009/0299184 A1* 12/2009 Walker et al. ................ 600/447

FOREIGN PATENT DOCUMENTS

JP   S58-069538 A   4/1983
JP   H07-095978 A   4/1995
(Continued)

OTHER PUBLICATIONS

Hirofumi Taki et al., "High Resolution Medical Acoustic Vascular Imaging Using Frequency Doman Interferometry", The Ninth lasted International Conference on Visualization, Imaging and Image Processing (VIIP 2009), Jul. 13, 2009, pp. 7-12.
(Continued)

*Primary Examiner* — Elmer Chao
(74) *Attorney, Agent, or Firm* — Canon USA, Inc. I.P. Division (57) ABSTRACT

A subject information obtaining apparatus includes a plurality of conversion elements configured to receive an elastic wave that has propagated from a subject and convert the elastic wave into a plurality of electrical signals, a frequency-domain interferometry adaptive processing unit configured to execute a frequency-domain interferometry method and adaptive signal processing using the plurality of electrical signals and obtain power intensity distribution by calculating power intensity at each position on a plurality of scan lines, and a correction unit configured to execute a correction process by which variation in power intensity between adjacent scan lines in a direction that intersects with the scan lines is reduced.

12 Claims, 7 Drawing Sheets

(51) Int. Cl.
    *A61B 8/08*     (2006.01)
    *G01S 7/52*     (2006.01)
    *G01S 15/89*     (2006.01)

(52) U.S. Cl.
    CPC ...... *G01S 7/52047* (2013.01); *G01S 15/8977* (2013.01); *A61B 8/0891* (2013.01)

(56) References Cited

FOREIGN PATENT DOCUMENTS

| | | |
|---|---|---|
| JP | 10-290801 A | 11/1998 |
| JP | H11-235341 A | 8/1999 |
| JP | 2004-195082 A | 7/2004 |
| JP | 2005-245479 A | 9/2005 |
| JP | 2010-183979 A | 8/2010 |

OTHER PUBLICATIONS

Medical Imaging Technology, Oct. 1994, p. 75.
Medical Imaging Technology, Sep. 2005, pp. 30 and 31.
Taki et al., High Range Resolution Medical Acoustic Vascular Imaging with Frequency Domain Interferometry, 32nd Annual Inter Conf Proc IEEE, Eng Med Bio Soc, 2010, 1, 5298-5301.

* cited by examiner

SUBJECT INFORMATION OBTAINING APPARATUS, METHOD FOR OBTAINING SUBJECT INFORMATION, AND COMPUTER-READABLE STORAGE MEDIUM

BACKGROUND OF THE INVENTION

Field of the Invention

The present invention relates to a subject information obtaining apparatus, a method for obtaining subject information, and a program, and more particularly to a technique for obtaining subject information by transmitting an elastic wave to a subject and receiving a wave reflected inside the subject.

Description of the Related Art

In general, in an ultrasonic diagnostic apparatus as a subject information obtaining apparatus, the spatial resolution in the depth direction when image data is formed by a pulse-echo method can be represented by an expression $(n\lambda)/2$, where $\lambda$ denotes the wavelength of an ultrasonic wave, which is an elastic wave, and n denotes the number of waves transmitted. For example, when two wavelengths of an ultrasonic wave having a center frequency of 12 MHz is transmitted, the spatial resolution in the depth direction is about 0.13 mm.

The pulse-echo method will be described. First, when an ultrasonic pulse has been transmitted to a subject, an ultrasonic wave is reflected and comes back in accordance with differences in acoustic impedance inside the subject. Next, the reflected wave is received and image data is generated using a received signal of the reflected wave. Typically, an envelope of the waveform of the received signal is obtained and converted into values of luminance, in order to generate the image data. By displaying an obtained image, luminance information on a scan line in a direction in which the ultrasonic wave is transmitted and received can be obtained. By obtaining the luminance information on each scan line for a plurality of times, that is, by repeating transmission and reception of an ultrasonic wave in a plurality of directions or positions in the subject, the inside of the subject can be imaged.

Although it is possible to realize a value of the spatial resolution in the depth direction of about 0.13 mm by using the pulse-echo method, higher values of spatial resolution are required. For example, if the layer structure of the blood vessel walls of a carotid artery can be observed in more detail, it is possible to contribute to early detection of arteriosclerosis or the like.

As techniques for improving the spatial resolution in the depth direction, a frequency-domain interferometry (FDI) method and a Capon method, which is a type of adaptive signal processing, are used in "Hirofumi Taki, Kousuke Taki, Takuya Sakamoto, Makoto Yamakawa, Tsuyoshi Shiina, and Toru Sato: Conf Proc IEEE Eng Med Biol Soc. 2010; 1: 5298-5301", in order to present results of imaging of the layer structure of blood vessel walls. By using the FDI method and the Capon method for received signals, it is possible to further improve the spatial resolution in the depth direction (scan line direction). However, a plurality of reflection layers are supposed to exist in a range (processing range) of a signal in the depth direction that has been cut out in order to execute the processing of the FDI method. In addition, it is probable that a plurality of waves reflected from reflection layers that are located close to one another have a high correlation. It is known that if the adaptive signal processing such as the Capon method is directly adopted for received signals of a plurality of such reflected waves that have a high correlation, unexpected effects such as cancellation of a desired signal can be produced. The effects caused by waves (coherent interference waves) that have a correlation can be reduced (suppressed) by using a frequency-averaging technique, and the FDI method and the Capon method can be adopted for the received signals of reflected waves.

However, if the FDI method and the adaptive signal processing are adopted for the received signals of reflected waves, how strongly coherent interference waves are suppressed does not match between adjacent scan lines, since the processing is executed for each scan line. It has been found that, as a result, it is possible that there are portions of obtained image data in which the continuity in a direction that intersects with the scan lines is insufficient.

On the other hand, the spatial resolution in the direction that intersects with the scan lines varies depending on convergence conditions at the times of transmission and reception of an elastic wave. In a general pulse-echo method, in order to complete imaging without missing minute reflection bodies in an observation region in a subject, distances between the scan lines (the intervals of the scan lines) are set to be shorter than the spatial resolution in the direction that intersects with the scan lines. Therefore, it can be concluded that if the FDI method and the adaptive signal processing are not used, the continuity between adjacent scan lines does not become insufficient.

That is, by using the FDI method and the adaptive signal processing, the continuity in the direction that intersects with the scan lines can become lower than that of a general image (an image generated by obtaining envelopes of received signals). Accordingly, a unique problem is caused that when continuity becomes lower, visibility also becomes lower.

SUMMARY OF THE INVENTION

A subject information obtaining apparatus according to an aspect of the present invention is a subject information obtaining apparatus that obtains information inside a subject by receiving an elastic wave that has propagated from the subject. The subject information obtaining apparatus includes a plurality of conversion elements configured to receive the elastic wave and convert the elastic wave into a plurality of electrical signals, a frequency-domain interferometry adaptive processing unit configured to execute a frequency-domain interferometry method and adaptive signal processing using the plurality of electrical signals and obtain power intensity distribution by calculating power intensity at each position on a plurality of scan lines, and a correction unit configured to execute a correction process by which variation in power intensity between adjacent scan lines in a direction that intersects with the scan lines is reduced.

According to embodiments of the present invention, it is possible to suppress a decrease in the visibility of an image caused by differences in how strongly coherent interference waves are suppressed between the scan lines.

Further features of the present invention will become apparent from the following description of exemplary embodiments with reference to the attached drawings.

DESCRIPTION OF THE EMBODIMENTS

Embodiments of the present invention will be described with reference to the drawings. An elastic wave herein is typically an ultrasonic wave, or may be an elastic wave called a sonic wave, an ultrasonic wave, or an acoustic wave. A subject information obtaining apparatus may be an apparatus that obtains subject information as image data by transmitting an elastic wave to a subject and receiving a wave (reflected elastic wave) reflected within the subject. The obtained subject information is information that reflects differences in acoustic impedance between tissues inside the subject.

Configuration of Subject Information Obtaining Apparatus in Present Invention

Figure 1:
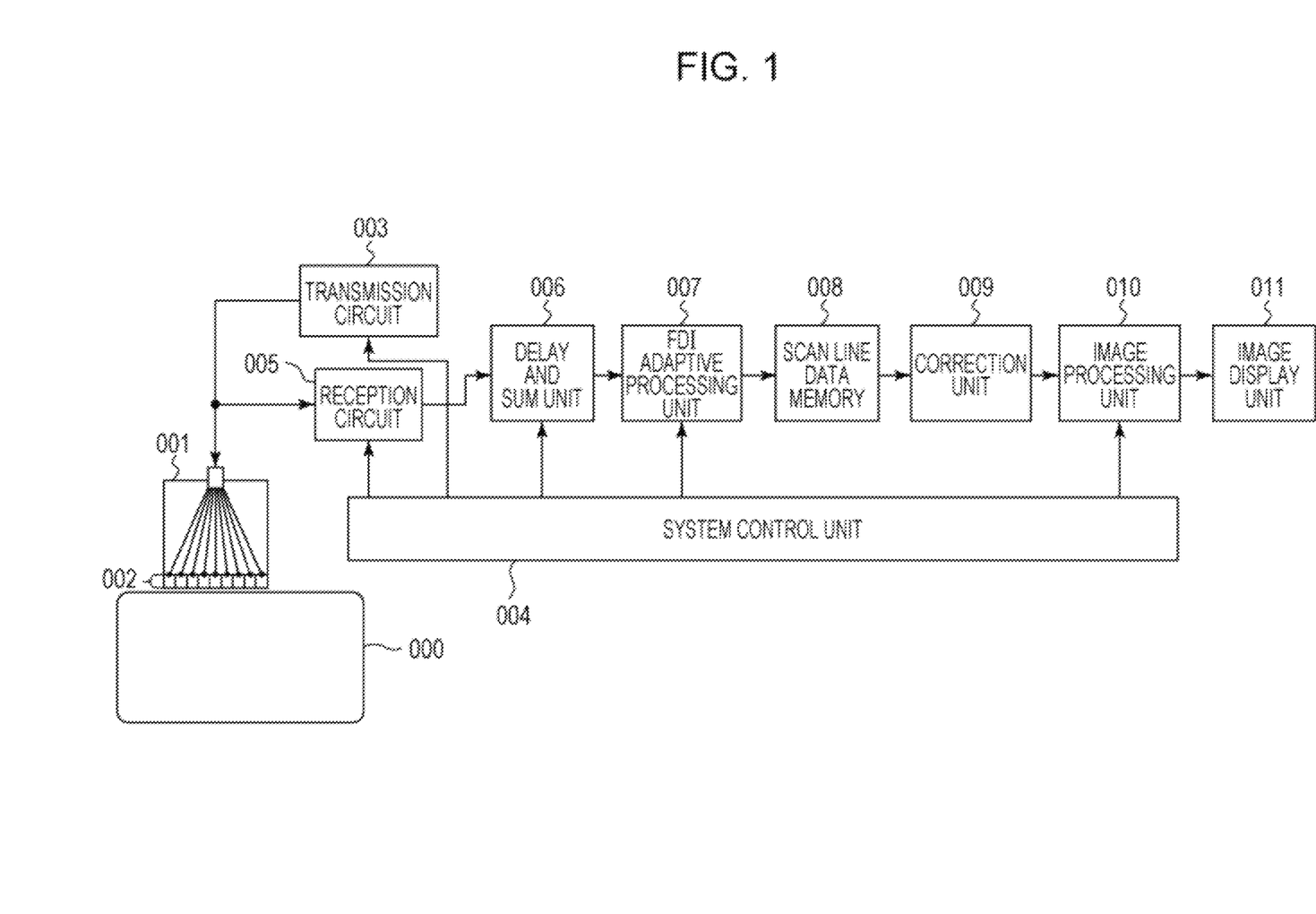
FIG. 1 is a schematic diagram illustrating the systematic overview of a subject information obtaining apparatus in the present invention.
Figure 2:
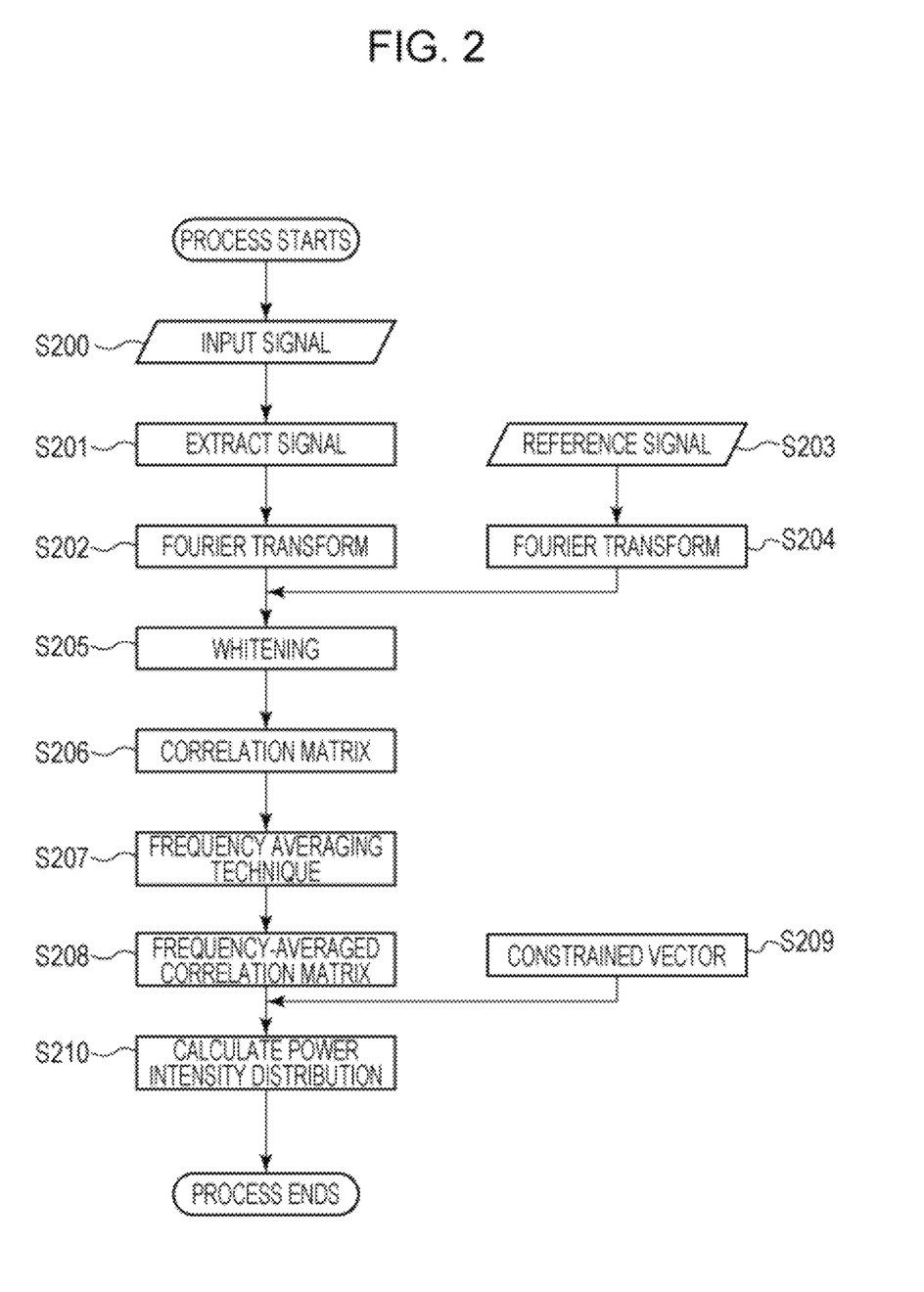
FIG. 2 is a flowchart illustrating a process executed in an FDI adaptive processing unit.

The configuration of the subject information obtaining apparatus in the present invention and details of a process when an FDI method and adaptive signal processing are used will be described with reference to FIGS. 1 and 2. FIG. 1 is a schematic diagram illustrating the systematic overview of a subject information obtaining apparatus according to an exemplary embodiment of the present invention. The subject information obtaining apparatus includes a probe 001 having a plurality of conversion elements 002, a reception circuit 005, a transmission circuit 003, a delay and sum unit 006, an FDI adaptive processing unit 007, a scan line data memory 008, a correction unit 009, an image processing unit 010, and a system control unit 004.

The transmission circuit 003 generates a transmission signal having a delay time and an amplitude according to a target position and a target direction in accordance with a control signal from the system control unit 004. The transmission signal is converted into an elastic wave by the plurality of conversion elements 002, and the elastic wave is transmitted to the inside of a subject 000. The elastic wave (reflected wave) reflected inside the subject 000 propagates through the subject 000. The elastic wave is then received by the plurality of conversion elements 002 and converted into a plurality of received signals (electrical signals). The received signals are input to the reception circuit 005. The reception circuit 005 amplifies the plurality of received signals and converts the plurality of received signals into a plurality of digital signals (digitized electrical signals). The digital signals output from the reception circuit 005 are input to the delay and sum unit 006. The delay and sum unit 006 executes a delay process on the plurality of digital signals in accordance with the directions and the positions of the transmission of the elastic wave, and adds the plurality of digital signals, that is, the delay and sum unit 006 executes a delay and sum process. The signals subjected to the delay and sum process are input to the FDI adaptive processing unit 007.

The FDI method is a method in which the received signals are divided in terms of frequencies and the phases of the divided signals are changed in accordance with target positions, in order to estimate the received power at the target positions. The amount of change in the phase can be predetermined based on the product of the distance from a certain reference position to a target position and the number of waves corresponding to the frequency.

In the adaptive signal processing, processing parameters are adaptively changed in accordance with the received signals. A Capon method, which is a type of the adaptive signal processing, is a method in which the plurality of input signals are processed such that the power is minimized while the sensitivity relative to the target positions remains the same. That is, in the process obtained by combining the FDI method and the adaptive signal processing, the received power at the target positions is estimated using, for the received signals that have been divided into frequency components, not the predetermined amount of change in the phase and weight but the amount of change in the phase and weight that have been calculated in accordance with the signals through the adaptive signal processing.

A process executed in the FDI adaptive processing unit 007 is described hereinafter with reference to FIG. 2. The FDI adaptive processing unit 007 receives a signal subjected to the delay and sum process as an input signal (S200). A signal corresponding to a period of time to be processed at a time, that is, a signal corresponding to a processing range, is extracted from the input signal (S201). The extracted signal is subjected to a Fourier transform and divided into frequency components Xsk (Xs1, Xs2, Xs3 . . . , and XsN) (S202).

A reference signal is input from the system control unit 004 (S203). The reference signal is then subjected to a Fourier transform and divided into frequency components Xrk (Xr1, Xr2, Xr3 . . . , and XrN) (S204). The reference signal is the signal waveform of a reflected wave that is assumed to be reflected from an interface (for example, a blood vessel wall) inside a subject and stored in the system control unit 004. The frequency components of the input signal and the reference signal are used in the following division in order to execute a whitening process (S205):

$$X_{wk} = \frac{X_{sk} X_{rk}^*}{|X_{rk}|^2 + \eta}$$

Here, $X_{wk}$ (1, 2 . . . , and N) denotes frequency components after the whitening process, $\eta$ denotes a minute number used for stabilization, and * denotes a complex conjugate. Next, a correlation matrix R is calculated using a vector X composed of the frequency components subjected to the whitening process (S206).

$$X = [X_{W1}, X_{W2} \ldots X_{WN}]^T R = XX^{T*}$$

Here, T denotes a transpose. The correlation matrix R is a matrix having a size of N×N.

Next, a frequency-averaging technique is used in which submatrices are extracted from the correlation matrix R and averaged (S207).

$$R' = \frac{1}{M} \sum_{m=1}^{M} R_m$$

$$R_{mij} = X_{w(i+m-1)} X_{w(j+m-1)*}$$

R' denotes a frequency-averaged correlation matrix and $R_m$ denotes the submatrices of the correlation matrix R having $R_{mij}$ as elements.

Thus, the frequency-averaged correlation matrix R' is calculated (S208).

Next, a constrained vector C is input (S209). The constrained vector C is a vector that changes in accordance with a position r in the processing range and defined by the following expression:

$$C=[\exp(jk_1 r), \exp(jk_2 r) \ldots, \exp(jk_{(N-M+1)} r)]$$

The power intensity distribution P(r) is calculated using the frequency-averaged correlation matrix R' and the constrained vector C (S210).

$$P(r) = \frac{1}{C^{T*}(R' + \eta' E)^{-1} C}$$

Θ'E denotes a diagonal matrix added to stabilize calculation of an inverse matrix.

As described above, in the FDI adaptive processing unit 007, the FDI method and the adaptive signal processing (here, the Capon method is used) are executed using the signals subjected to the delay and sum process as input signals, and the power intensity distribution is output. In the present exemplary embodiment, the obtained power intensity distribution indicates subject information that reflects differences in acoustic impedance between tissues inside the subject.

The output power intensity distribution is saved to the scan line data memory 008. Thus, received signals for one operation for transmitting an elastic wave are processed, and the power intensity distribution for one scan line is calculated and saved. By repeating this operation, the power intensity distribution of a plurality of scan lines is saved to the scan line data memory 008.

The correction unit 009 executes correction, using the power intensity distribution of the plurality of scan lines output from the scan line data memory 008 as an input, such that the continuity of the power intensity distribution in a direction (typically a direction perpendicular to the scan lines) that intersects with the scan lines increases. That is, the correction unit 009 executes a correction process by which variation in power intensity between adjacent scan lines is reduced in the direction that intersects with the scan lines. In accordance with instructions from the system control unit 004, the image processing unit 010 executes various types of image processing such as edge reinforcement and contrast adjustment using the corrected power intensity distribution of the plurality of scan lines as an input, and outputs luminance data (image data). An image display unit 011 displays the input luminance data as an image. The image display unit 011 may be provided separately from the subject information obtaining apparatus.

Figure 3:
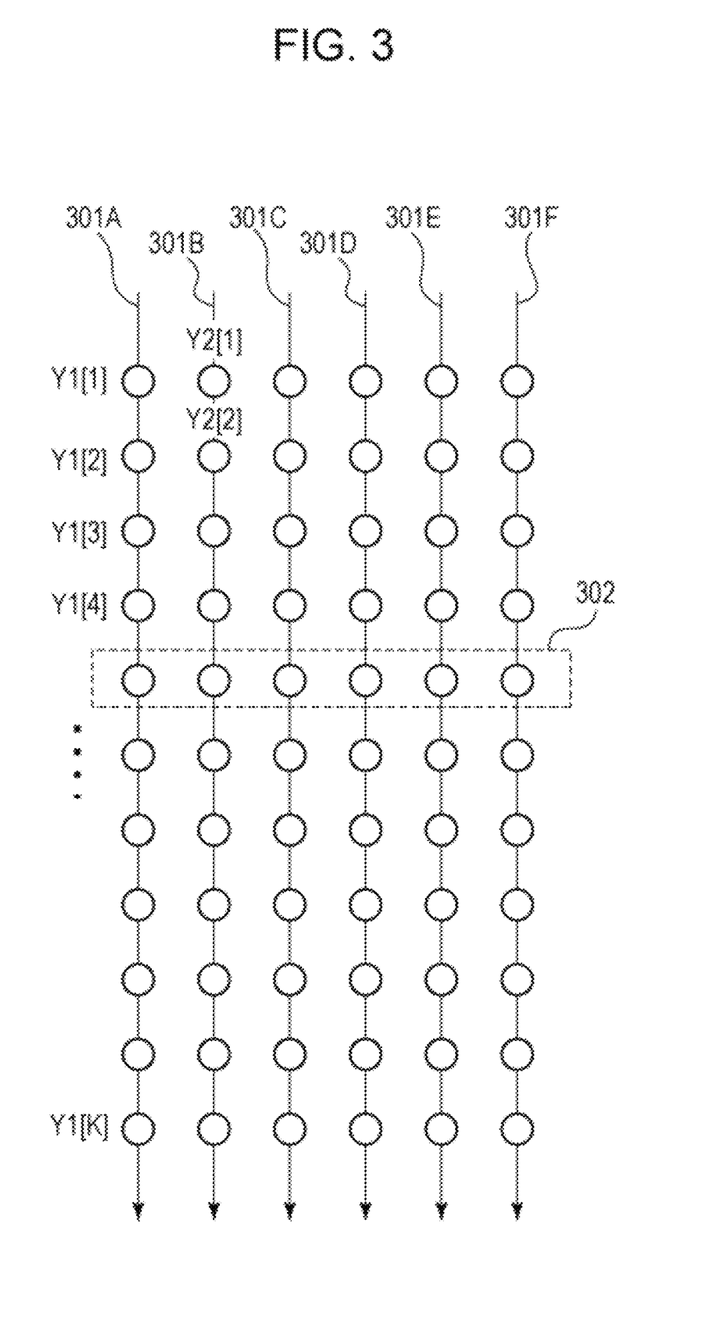
FIG. 3 is a diagram schematically illustrating the positions of a plurality of scan lines.

The concept of the operation of the correction unit 009 is described with reference to FIG. 3. FIG. 3 is a diagram schematically illustrating the power intensity distribution on scan lines 301A to 301F. Hollow circles on the scan lines 301A to 301F indicate power intensities at respective positions thereof. As described above, spatial resolution in the direction (the horizontal direction in FIG. 3) that intersects with scan lines is generally higher (longer) than distances between the scan lines. That is, variation in the distribution of power intensities (for example, power intensities 302) in the direction that intersects with the scan lines is small. However, when the FDI method and the adaptive signal processing are used, the continuity of power intensities in the direction that intersects with the scan lines can be low since how strongly coherent interference waves are suppressed differs between the scan lines. The correction unit 009 executes correction on power intensities in the direction that intersects with the scan lines 301A to 301F such that variation in power intensity between adjacent scan lines becomes small, in order to improve continuity.

Thus, by increasing the continuity in the direction that intersects with the scan lines, the spatial resolution in the scan line direction is improved when the FDI method and the adaptive signal processing are used, as well as a decrease in the visibility of an image being suppressed, thereby making it possible to obtain a more stable image whose visibility is high.

The number of scan lines on which correction is to be executed (that is, the number of power intensities on which correction is to be executed) can be changed in accordance with convergence conditions at the times of transmission and reception of an elastic wave. By executing the correction, the resolution in the direction that intersects with the scan lines decreases. Therefore, a larger number of scan lines on which the correction is to be executed is not necessary desirable.

The spatial resolution in the direction that intersects with the scan lines changes depending on the convergence conditions of an elastic wave. If the wavelength of an elastic wave is assumed to be λ, the open intervals of the plurality of conversion elements are assumed to be D, and the distance in the depth direction (scan line direction) is assumed to be z, the convergence width can be represented by an expression 1.22(λ/D)z. That is, the spatial resolution in the direction that intersects with the scan lines is determined by the wavelength λ, the open intervals D, and the distance z in the depth direction.

Therefore, when the spatial resolution determined by the convergence conditions (setting conditions of the wavelength λ, the open intervals D, and the distance z in the depth direction) has been changed, the number of power intensities on which correction is to be executed can also be changed. More specifically, the number of power intensities on which correction is to be executed can be set to a number less than or equal to twice the spatial resolution in the direction that intersects with the scan lines. The number of power intensities on which correction is to be executed can be set to a number less than or equal to the spatial resolution in the direction that intersects with the scan lines.

Although a process adopting the Capon method has been described above, the above-described process can be applied to other types of adaptive signal processing that require the frequency-averaging technique in order to suppress the effects of coherent interference waves, such as multiple signal classification (MUSIC) and estimation of signal parameters via rotational invariant techniques (ESPRIT).

Subject information obtaining apparatuses according to the embodiments of the present invention will be described hereinafter in detail with reference to the drawings.

First Exemplary Embodiment

A first exemplary embodiment is a mode in which processing is executed using the system illustrated in FIG. 1. The operation of the system is as described above, and therefore description thereof is omitted. The operation of the correction unit 009 will be described.

The correction unit 009 according to the present embodiment executes a correction process on the input power intensity distribution of the plurality of scan lines. Signals input to the correction unit 009 indicating L scan lines each having information regarding K power intensities are expressed as follows:

$$Y1[s], Y2[s] \ldots, YL[s](s=1,2\ldots,K)$$

The positional relationships of the power intensities are as illustrated in FIG. 3.

In order to execute a correction process by which variation in power intensity between adjacent scan lines in the direction that intersects with the scan lines is reduced, the correction unit 009 first extracts power intensities (for example, Y1[5], Y2[5], Y3[5], and so on) in the direction that intersects with the scan lines. In the present embodiment, a correction process represented by the following expression is executed in order to obtain new power intensity Yk'. It is to be noted that hi is a coefficient that is separately set.

$$Y'_k[s] = \frac{1}{\sum_{i=0}^{w-1} h_i} \sum_{i=0}^{w-1} (h_i \times Y_{k-i}[s])$$

Figure 4A:
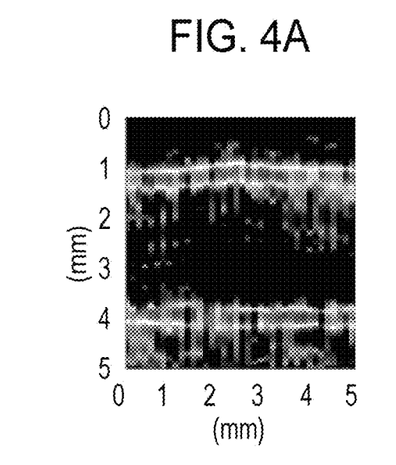
FIGS. 4A to 4C are diagrams illustrating effects obtained by a correction process according to a first embodiment.
Figure 4B:
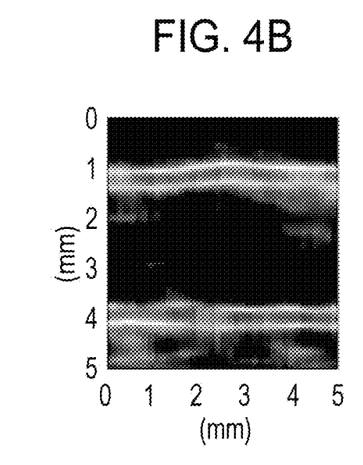
Figure 4C:
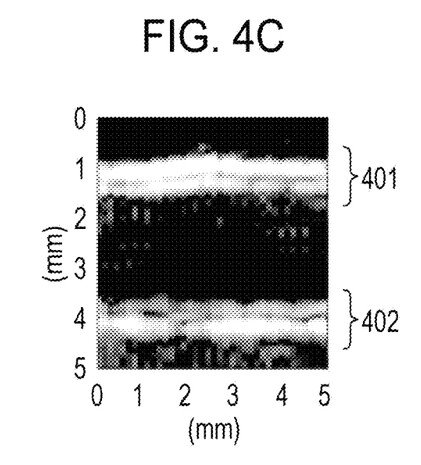

FIGS. 4A to 4C are diagrams illustrating effects obtained by the correction process executed by the correction unit 009 according to the present embodiment. The vertical axis represents the distance in the depth direction (scan line direction), and the horizontal axis represents the distance in the direction that intersects with the scan lines. FIGS. 4A to 4C illustrate images of blood vessel walls of a femoral artery of a pig obtained by receiving waves reflected from the femoral artery. FIG. 4C illustrates an image (a so-called B-mode image) of the femoral artery of the pig obtained by detecting envelopes of received signals. Portions 401 and 402 illustrated in FIGS. 4A to 4C are the blood vessel walls of the femoral artery. FIG. 4A illustrates an image obtained by applying the FDI method and the Capon method to the received signals. Although the spatial resolution in the scan line direction (vertical direction of the image) is improved, there are portions in which continuity is insufficient in the direction (horizontal direction of the image) that intersects with the scan lines, since how strongly coherent interference waves are suppressed differs between the scan lines.

FIG. 4B illustrates an image obtained by executing a correction process using the correction unit 009 according to this embodiment and coefficients of h0=h1=h2=h3=h4=1 and w=5. The spatial resolution in the scan line direction (vertical direction of the image) is higher than that in the image illustrated in FIG. 4C, and the continuity in the direction (horizontal direction of the image) that intersects with the scan lines is higher than that in the image illustrated in FIG. 4A. Visibility is thus improved.

Figure 5:
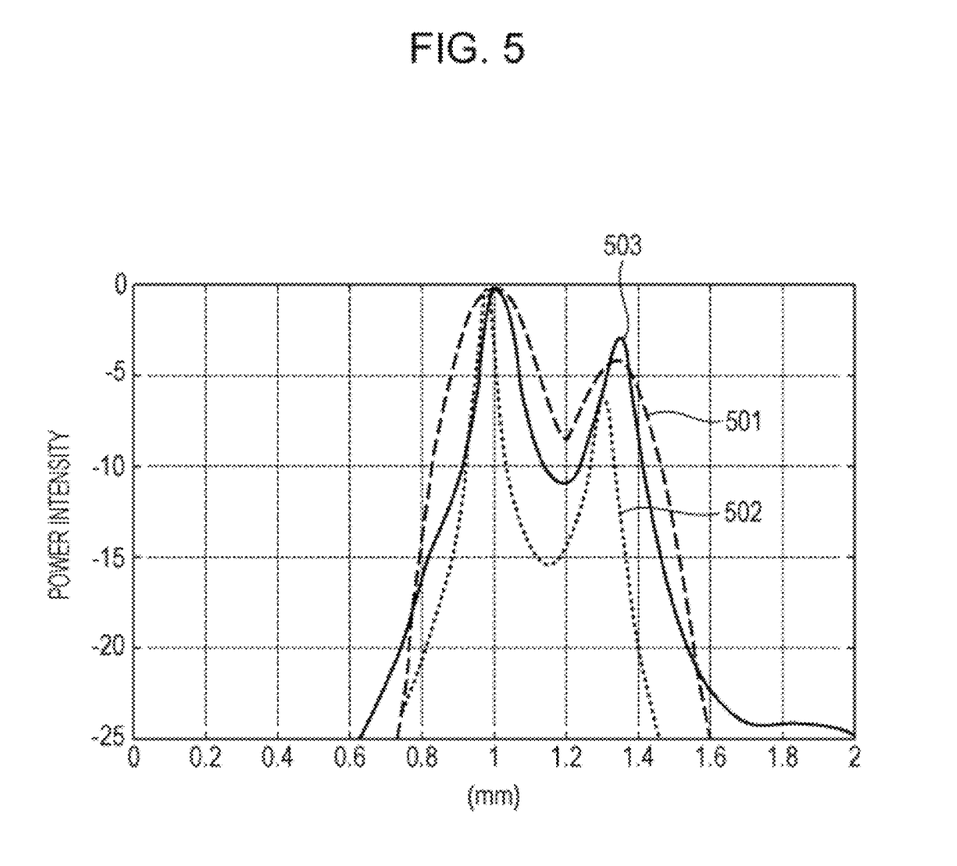
FIG. 5 is a graph illustrating power intensity distribution according to the first embodiment.

FIG. 5 is a graph obtained by plotting the power intensity distribution of a single scan line (vertical direction of each image) in each of the images illustrated in FIGS. 4A to 4C. A curve 501 indicates the power intensity distribution of the B-mode image obtained by detecting an envelope, a curve 502 indicates the power intensity distribution of the image obtained by adopting the FDI method and Capon method, and a curve 503 indicates the power intensity distribution of the image obtained by executing the process according to this embodiment. As can be seen from FIG. 5, the resolution of the image obtained by applying the present embodiment in the scan line direction is higher than that of the general B-mode image.

As described above, according to the present embodiment, it is possible, by using the FDI method and the Capon method, to improve the spatial resolution in the scan line direction and to provide stable image data whose continuity in the direction that intersects with the scan lines is high.

The correction process executed by the correction unit 009 according to the present embodiment serves as a finite impulse response (FIR) filter that executes smoothing on the power intensity distribution in the direction that intersects with the scan lines. The same effects can be obtained regardless of coefficients used, such as those having a uniform (rectangular) shape or other coefficients including those having a triangular shape, a trapezoidal shape, or a Gaussian shape, so long as functions as a smoothing filter are realized.

Second Exemplary Embodiment

A second exemplary embodiment is also a specific mode in which processing is executed using the system illustrated in FIG. 1. The operation of the system is as described above, and therefore description thereof is omitted. The operation of the correction unit 009 will be described. The correction unit 009 according to the present embodiment executes a correction process represented by the following expression on the input power intensity distribution of the plurality of scan lines.

$$Y''_k[s] = \sum_{j=1}^{w'} (a_j \times Y'_{k-j}[s]) + \sum_{i=0}^{w-1} (b_i \times Y_{k-i}[s])$$

Figure 6:
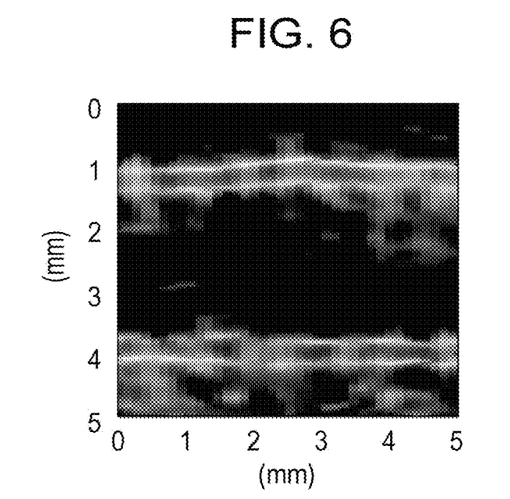
FIG. 6 is a diagram illustrating effects obtained by a correction process according to a second embodiment.

FIG. 6 illustrates an image obtained by executing the processing using the correction unit 009 according to this embodiment and coefficients of [a1, a2, a3, a4, a5, a6]=[1, 0, 0.6334, 0, 0.0557, 0] and [b0, b1, b2, b3, b4, b5]=[0.0528, 0.2639, 0.5279, 0.2639, 0.0528]. As can be seen from FIG. 6, the spatial resolution in the scan line direction (vertical direction of the image) is higher than that of the general B-mode image (FIG. 4C), and the continuity in the direction (horizontal direction of the image) that intersects with the scan lines is higher than that of the image illustrated in FIG. 4A. Visibility is thus improved.

As described above, according to the present embodiment, it is possible, by using the FDI method and the Capon method, to improve the spatial resolution in the scan line direction and to provide stable image data whose continuity in the direction that intersects with the scan lines is high. The correction process executed by the correction unit 009 according to this embodiment serves as an infinite impulse response (IIR) filter that executes smoothing on the power intensity distribution in the direction that intersects with the scan lines. The same effects can be obtained regardless of coefficients used, so long as functions as a smoothing filter are realized. Thus, by using the IIR filter in the correction process, it is possible to execute the correction process while realizing more appropriate filter characteristics with a smaller calculation load (a small number of coefficients used in the calculation).

Third Exemplary Embodiment

A third exemplary embodiment is also a mode in which processing is executed using the system illustrated in FIG. 1. The operation of the system is as described above, and therefore description thereof is omitted. The operation of the correction unit 009 will be described.

The correction unit 009 according to the present embodiment receives the power intensity distribution of the plurality of scan lines and then extracts NX power intensities (for example, Y1[5], Y2[5], Y3[5], and so on) in the direction that intersects with the scan lines. The NX power intensities are rearranged in order of intensity. If NX is an even number, an (NX/2+1)th power intensity is output, and if NX is an odd number, an ((NX+1)/2)th power intensity is output in the correction process.

Figure 7:
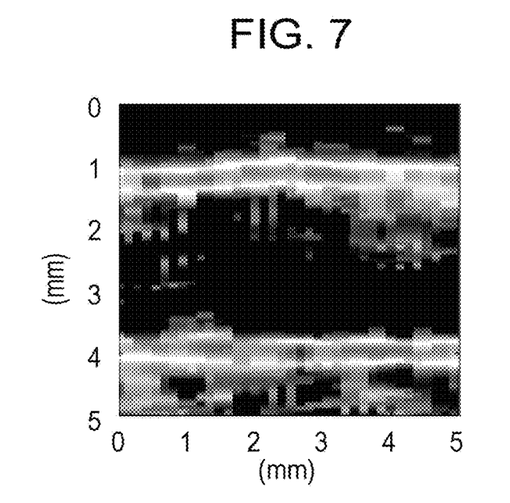
FIG. 7 is a diagram illustrating effects obtained by a correction process according to a third embodiment.

FIG. 7 illustrates an image obtained by executing the correction process using the correction unit 009 according to the present embodiment and NX=3. The spatial resolution in the scan line direction (vertical direction of the image) is higher than that of the general B-mode image (FIG. 4C), and the continuity in the direction (horizontal direction of the image) that intersects with the scan lines is higher than that of the image illustrated in FIG. 4A. Visibility is thus improved.

As described above, according to the present embodiment, it is possible, by using the FDI method and the Capon method, to improve the spatial resolution in the scan line direction and to provide stable image data whose continuity in the direction that intersects with the scan lines is high. The correction process executed by the correction unit 009 according to the present embodiment serves as a median filter for the power intensity distribution in the direction that intersects with the scan lines, and correction effects can be obtained as a result of smoothing.

Fourth Exemplary Embodiment

A fourth exemplary embodiment is also a mode in which processing is executed using the system illustrated in FIG. 1. The operation of the system is as described above, and therefore description thereof is omitted. The operation of the correction unit 009 will be described.

After the power intensity distribution of the plurality of scan lines is input, the correction unit 009 according to the present embodiment extracts NX power intensities (for example, Y1[5], Y2[5], Y3[5], and so on) in the direction that intersects with the scan lines. The NX power intensities are subjected to a Fourier transform and a low-pass filter that blocks frequencies higher than a certain frequency is used.

By using this low-pass filter, high-frequency components can be removed in the direction that intersects with the scan lines. That is, variation in power intensity between adjacent scan lines in the direction that intersects with the scan lines can be reduced.

As described above, according to the present embodiment, as with the first to third embodiments, it is possible, by using the FDI method and the Capon method, to improve the spatial resolution in the scan line direction and to provide a stable image whose continuity in the direction that intersects with the scan lines is high.

Fifth Exemplary Embodiment

Figure 8:
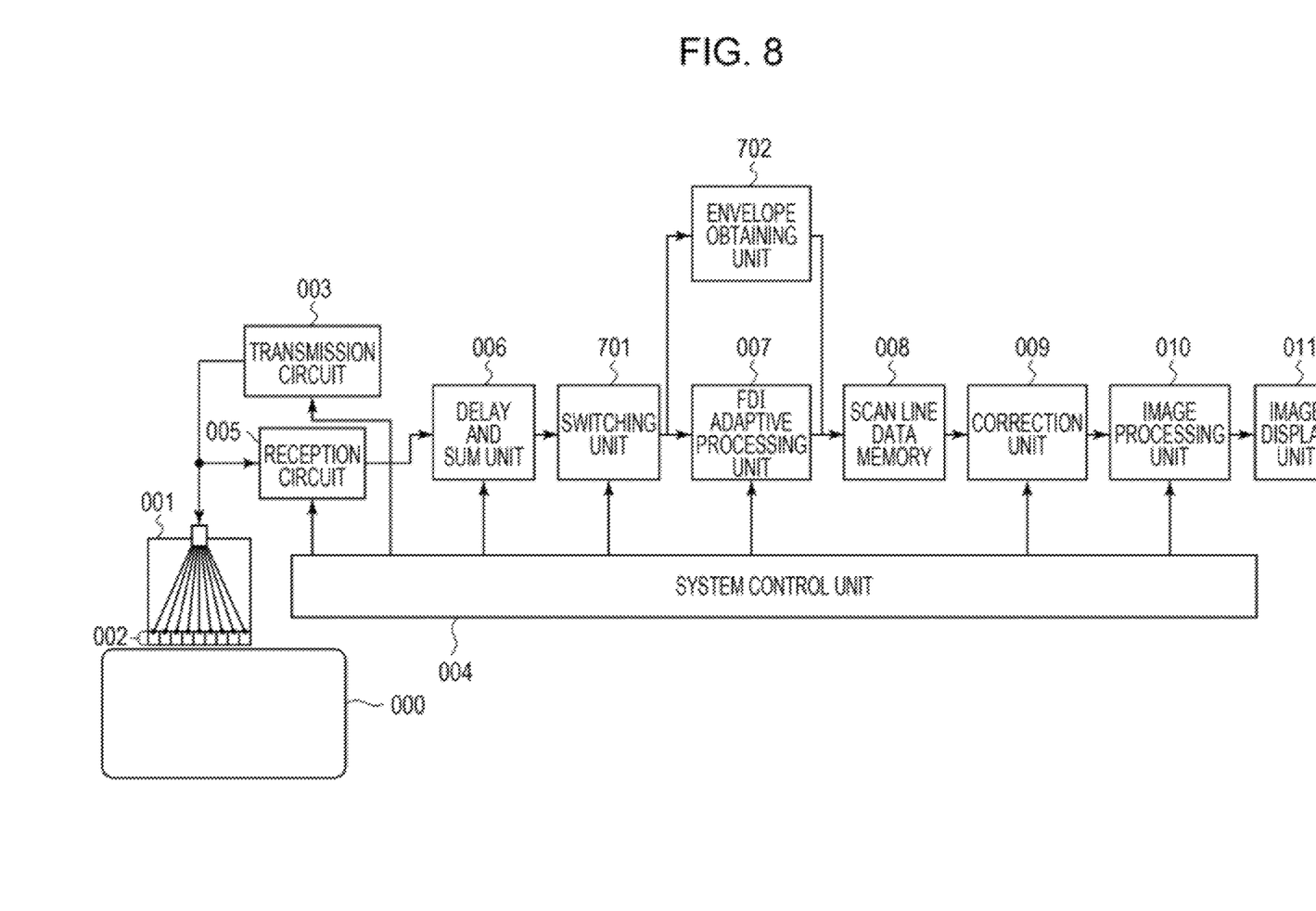
FIG. 8 is a schematic diagram illustrating the systematic overview of a subject information obtaining apparatus according to a fifth embodiment.

The fifth exemplary embodiment includes a switching unit that switches a target to which the signals subjected to the delay and sum process are to be input. FIG. 8 is the systematic overview of a subject information obtaining apparatus according to the present embodiment. Only differences from the first to fourth embodiments will be described.

The subject information obtaining apparatus according to the present embodiment further includes, in addition to the configuration illustrated in FIG. 1, a switching unit 701 and an envelope obtaining unit 702. The process until an elastic wave is transmitted and received and the delay and sum process is executed is the same as those according to the first to fourth embodiments. In the present embodiment, the signals subjected to the delay and sum process in the delay and sum unit 006 are input to the switching unit 701. The switching unit 701 outputs the input signals to the envelope obtaining unit 702 or the FDI adaptive processing unit 007 in accordance with an instruction from the system control unit 004.

First, an operation to be executed when the switching unit 701 has output the signals subjected to the delay and sum process only to the envelope obtaining unit 702 will be described. The envelope obtaining unit 702 obtains envelopes of the input signals and outputs the envelopes to the scan line data memory 008 as envelope data. The scan line data memory 008 and the correction unit 009 transmit the envelope data without processing the envelope data, and finally the image processing unit 010 receives the envelope data. The image processing unit 010 executes various types of image processing such as edge reinforcement and contrast adjustment in accordance with instructions from the system control unit 004, and outputs luminance data (image data). The image display unit 011 displays the input luminance data as an image.

Next, an operation to be executed when the switching unit 701 has output the signals subjected to the delay and sum process only to the FDI adaptive processing unit 007. In this case, as with the first to fourth embodiments, the FDI adaptive processing unit 007, the scan line data memory 008, and the correction unit 009 execute a correction process by which the continuity in a direction in which the scan lines are adjacent to one another is improved.

As described above, control is executed such that the correction unit 009 does not operate for the envelope data, but operates for the power intensity distribution processed by the FDI adaptive processing unit 007, in order to correct the power intensity distribution such that the power intensity distribution becomes continuous. However, in the present embodiment, the switching unit 701 and the envelope obtaining unit 702 may be connected to each other. In this case, the envelope data is directly input to the image processing unit 010.

The system according to the present embodiment can be set such that the system control unit 004 issues an instruction to the switching unit 701 in accordance with, for example, a specific instruction from an operator or an image capture mode selected by the operator. By setting the system in this manner, it is possible to focus upon the spatial resolution in the depth direction (when, for example, the thicknesses of the blood vessel walls of a carotid artery are to be measured) and to compare an image with a general B-mode image (an image obtained by detecting envelopes).

In addition, in accordance with instructions from the system control unit 004, it is possible not to execute an excessive correction process on a B-mode image that already has continuity and to execute the correction process on image data that has been obtained by using the FDI method and the adaptive signal processing and that has portions in which continuity is insufficient.

Aspects of the above-described embodiments can be realized by executing the following process. That is, in this process, software (a program) that realizes the functions of each embodiment described above is supplied to a system or an apparatus through a network or various recording media, and a computer (or a central processing unit (CPU) or a microprocessor unit (MPU)) in the system or the apparatus reads the program.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-086511 filed Apr. 8, 2011, which is hereby incorporated by reference herein in its entirety.

What is claimed is:

1. A subject information obtaining apparatus that obtains information inside a subject by receiving an elastic wave that has propagated from the subject, the subject information obtaining apparatus comprising:
   a plurality of conversion elements configured to receive the elastic wave and convert the elastic wave into a plurality of electrical signals;
   an envelope obtaining processor that obtains envelopes using the electrical signals subjected to a delay and sum process;
   a frequency-domain interferometry adaptive processor that executes a frequency-domain interferometry method and adaptive signal processing using the plurality of electrical signals and obtains a power intensity distribution by calculating a power intensity at each position on a plurality of scan lines, the scan lines extending in a depth direction of the subject;
   a correction processor that executes selectively, in a case the power intensity distribution obtained by the frequency-domain interferometry adaptive processor is input, a correction process on the power intensities obtained by the frequency-domain interferometry adaptive processor to obtain a post-correction power intensity distribution in which difference in power intensities between two adjacent scan lines has been reduced compared to difference in power intensities between the two adjacent scan lines before applying the correction process; and
   an image processor that generates image data based on the envelopes or the post-correction power intensity distribution.

2. The subject information obtaining apparatus according to claim 1,
   wherein, the correction processor, in the correction process, further uses a smoothing filter for power intensity distribution in the direction that intersects with the scan lines.

3. The subject information obtaining apparatus according to claim 1,
   wherein, the correction processor, in the correction process, further uses a median filter for power intensity distribution in the direction that intersects with the scan lines.

4. The subject information obtaining apparatus according to claim 1,
   wherein, the correction processor, in the correction process, further uses a low-pass filter for power intensity distribution in the direction that intersects with the scan lines.

5. The subject information obtaining apparatus according to claim 1,
   wherein the correction processor further executes the correction process on different numbers of power intensities, in accordance with convergence conditions of transmission and reception of the elastic wave.

6. The subject information obtaining apparatus according to claim 1, further comprising:
   a delay and sum processor that executes a delay and sum process on the plurality of electrical signals,
   wherein the frequency-domain interferometry adaptive processor further executes the frequency-domain interferometry method and the adaptive signal processing using the electrical signals subjected to the delay and sum process.

7. The subject information obtaining apparatus according to claim 6, further comprising:
   a switch that switches a target to which the electrical signals subjected to the delay and sum process are to be input between the frequency-domain interferometry adaptive processor and the envelope obtaining processor.

8. A subject information obtaining apparatus that obtains information inside a subject using a plurality of electrical signals obtained by receiving an elastic wave that has propagated from the subject comprising:
   an envelope obtaining processor that obtains envelopes using the electrical signals subjected to a delay and sum process;
   a frequency-domain interferometry adaptive processor that executes a frequency-domain interferometry method and adaptive signal processing using the plurality of electrical signals and obtains a power intensity distribution by calculating a power intensity at each position on a plurality of scan lines, the scan lines extending in a depth direction of the subject;
   a correction processor that executes selectively, in a case the power intensity distribution obtained by the frequency-domain interferometry adaptive processor is input, a correction process on the power intensities obtained by the frequency-domain interferometry adaptive processor to obtain a post-correction power intensity distribution in which difference in power intensities between two adjacent scan lines has been reduced compared to difference in power intensities between the two adjacent scan lines before applying the correction process; and
   an image processor that generates image data based on the envelopes or the post-correction power intensity distribution.

9. The subject information obtaining apparatus according to claim 8,
   wherein, the correction processor, in the correction process, further uses a smoothing filter for power intensity distribution in the direction that intersects with the scan lines.

10. The subject information obtaining apparatus according to claim 8,
  wherein the correction processor further executes the correction process on different numbers of power intensities, in accordance with convergence conditions of transmission and reception of the elastic wave.

11. The subject information obtaining apparatus according to claim 8, further comprising:
  a delay and sum processor that executes a delay and sum process on the plurality of electrical signals,
  wherein the frequency-domain interferometry adaptive processor further executes the frequency-domain interferometry method and the adaptive signal processing using the electrical signals subjected to the delay and sum process.

12. The subject information obtaining apparatus according to claim 11, further comprising:
  a switch that switches a target to which the electrical signals subjected to the delay and sum process are to be input between the frequency-domain interferometry adaptive processor and the envelope obtaining processor.

* * * * *